United States Patent
Fukuda

(10) Patent No.: US 10,810,766 B2
(45) Date of Patent: Oct. 20, 2020

(54) IMAGE PROCESSING APPARATUS, IMAGE PROCESSING METHOD, AND IMAGE PROCESSING PROGRAM

(71) Applicant: FUJIFILM CORPORATION, Minato-ku, Tokyo (JP)

(72) Inventor: Wataru Fukuda, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 119 days.

(21) Appl. No.: 16/109,763

(22) Filed: Aug. 23, 2018

(65) Prior Publication Data
US 2019/0096098 A1      Mar. 28, 2019

(30) Foreign Application Priority Data

Sep. 28, 2017   (JP) ................. 2017-187890

(51) Int. Cl.
*G06K 9/00* (2006.01)
*G06T 11/00* (2006.01)
(Continued)

(52) U.S. Cl.
CPC ............ *G06T 11/006* (2013.01); *A61B 6/025* (2013.01); *A61B 6/502* (2013.01); *A61B 6/5205* (2013.01);
(Continued)

(58) Field of Classification Search
CPC ......... G06T 11/006; G06T 5/40; G06T 5/008; G06T 2207/30068; G06T 2207/10081; G06T 2211/421; A61B 6/025
See application file for complete search history.

(56) References Cited

U.S. PATENT DOCUMENTS

| 4,149,080 A | * | 4/1979 | Schittenhelm | ....... | A61B 6/4085 |
| | | | | | 250/369 |
| 4,472,823 A | * | 9/1984 | Waltham | ................ | A61B 6/032 |
| | | | | | 378/19 |

(Continued)

FOREIGN PATENT DOCUMENTS

| JP | 2005-065856 A | 3/2005 |
| JP | 2008-114064 A | 5/2008 |

(Continued)

OTHER PUBLICATIONS

English language translation of the following: Office action dated Aug. 25, 2020 from the JPO in a Japanese patent application No. 2017-187890 corresponding to the instant patent application. This office action translation is submitted now in order to supplement the understanding of the cited references which are being disclosed in the instant Information Disclosure Statement.

*Primary Examiner* — Amir Alavi

(74) *Attorney, Agent, or Firm* — Solaris Intellectual Property Group, PLLC

(57) ABSTRACT

In a console according to an embodiment, a control unit functions as a generation unit that generates a tomographic image from a plurality of projection images, which have been captured by a radiation detector at each of a plurality of imaging positions with different irradiation angles, with radiation sequentially emitted from each of the plurality of
(Continued)

imaging positions, using a reconstruction process. In addition, the control unit functions as a derivation unit that derives the degree of enhancement as a parameter value used in a frequency enhancement process which is an example of image processing for a tomographic image, on the basis of the image analysis result of a projection image corresponding to an irradiation angle of 0 degrees. Furthermore, the control unit functions as a correction unit that corrects the parameter value according to image processing used in the reconstruction process and an image processing unit that performs the image processing on a tomographic image on the tomographic image using the corrected parameter value.

10 Claims, 8 Drawing Sheets

(51) Int. Cl.
  *G06T 5/40*   (2006.01)
  *G06T 5/00*   (2006.01)
  *A61B 6/02*   (2006.01)
  *A61B 6/00*   (2006.01)
  *A61B 6/04*   (2006.01)

(52) U.S. Cl.
  CPC ............ *G06T 5/008* (2013.01); *G06T 5/40* (2013.01); *A61B 6/0414* (2013.01); *G06T 2207/10081* (2013.01); *G06T 2207/30068* (2013.01); *G06T 2211/421* (2013.01); *G06T 2211/436* (2013.01)

(56) References Cited

U.S. PATENT DOCUMENTS

| | | | | |
|---|---|---|---|---|
| 4,707,786 | A * | 11/1987 | Dehner | G06T 11/005 378/14 |
| 4,809,172 | A * | 2/1989 | Hopkinson | G06T 11/005 378/4 |
| 6,925,140 | B2 * | 8/2005 | Bruder | A61B 6/4233 378/19 |
| 7,085,345 | B2 * | 8/2006 | Nukui | A61B 6/032 378/147 |
| 7,190,758 | B2 * | 3/2007 | Hagiwara | A61B 6/032 378/7 |
| 7,260,169 | B2 * | 8/2007 | Bernhardt | A61B 6/032 378/19 |
| 7,409,034 | B2 * | 8/2008 | Gohno | A61B 6/032 378/15 |
| 7,636,415 | B2 * | 12/2009 | Popescu | A61B 6/032 378/7 |
| 9,146,327 | B2 * | 9/2015 | Suppes | G01T 7/005 |
| 10,126,445 | B2 * | 11/2018 | Hashizume | G01T 1/2985 |
| 2005/0053188 | A1 * | 3/2005 | Gohno | A61B 6/032 378/15 |
| 2015/0302615 | A1 | 10/2015 | Fukuda | |
| 2015/0332485 | A1 | 11/2015 | Klausz et al. | |
| 2019/0096098 | A1 * | 3/2019 | Fukuda | G06T 11/006 |

FOREIGN PATENT DOCUMENTS

| | | |
|---|---|---|
| JP | 2013-031641 A | 2/2013 |
| JP | 2013-144097 A | 7/2013 |
| JP | 2014-133095 A | 7/2014 |

* cited by examiner

IMAGE PROCESSING APPARATUS, IMAGE PROCESSING METHOD, AND IMAGE PROCESSING PROGRAM

CROSS REFERENCE TO RELATED APPLICATIONS

The present application claims priority under 35 U.S.C. § 119 to Japanese Patent Application No. 2017-187890 filed on Sep. 28, 2017. The above application is hereby expressly incorporated by reference, in its entirety, into the present application.

BACKGROUND OF THE INVENTION

Field of the Invention

The present invention relates to an image processing apparatus, an image processing method, and an image processing program.

Related Art

As a radiography method, so-called tomosynthesis imaging has been known which sequentially emits radiation from each of a plurality of imaging positions with different irradiation angles and captures a plurality of projection images at each imaging position using a radiation detector. In tomosynthesis imaging, a tomographic image is generated from a plurality of captured projection images by a reconstruction process.

In general, predetermined image processing, such as a frequency enhancement process or a gradation process, is performed on a radiographic image interpreted by a user, such as a technician, in order to assist the user's interpretation. Therefore, the predetermined image processing is also performed on a tomographic image. For example, JP2008-114064A and JP2013-144097A disclose a technique that performs predetermined image processing for a tomographic image using a parameter obtained on the basis of a projection image.

However, the tomographic image is an image affected by the reconstruction process unlike the projection image. Therefore, in a case in which the parameter obtained on the basis of the projection image is applied to the tomographic image as in the technique disclosed in JP2008-114064A and JP2013-144097A, an image with desired image quality is not obtained by the influence of the reconstruction process and the image quality of the tomographic image is likely to deteriorate.

SUMMARY

The present disclosure has been made in view of the above-mentioned problems and an object of the present disclosure is to provide an image processing apparatus, an image processing method, and an image processing program that can prevent the deterioration of the image quality of a tomographic image.

In order to achieve the object, according to the present disclosure, there is provided an image processing apparatus comprising: a generation unit that generates a tomographic image from a plurality of projection images, which have been captured by a radiation detector at each of a plurality of imaging positions with different irradiation angles, with radiation sequentially emitted from each of the plurality of imaging positions, using a reconstruction process; a derivation unit that derives a parameter value used in predetermined image processing which is performed on the tomographic image, on the basis of an image analysis result of at least one of the plurality of projection images; a correction unit that corrects the parameter value according to image processing used in the reconstruction process; and an image processing unit that performs the predetermined image processing on the tomographic image using the parameter value corrected by the correction unit.

In order to achieve the object, according to the present disclosure, there is provided an image processing apparatus comprising: a generation unit that generates a tomographic image from a plurality of projection images, which have been captured by a radiation detector at each of a plurality of imaging positions with different irradiation angles, with radiation sequentially emitted from each of the plurality of imaging positions, using a reconstruction process; a derivation unit that derives a parameter value used in predetermined image processing which is performed on the tomographic image, on the basis of an image analysis result after image processing used in the reconstruction process is performed on at least one of the plurality of projection images; and an image processing unit that performs the predetermined image processing on the tomographic image using the parameter value.

In the image processing apparatus according to the present disclosure, the reconstruction process may be performed by a filtered back projection method and the image processing used in the reconstruction process may be a filtering process in the filtered back projection method.

In the image processing apparatus according to the present disclosure, the predetermined image processing may be at least one of a frequency enhancement process or a gradation conversion process.

In the image processing apparatus according to the present disclosure, the derivation unit may derive a feature amount from a cumulative histogram which is the image analysis result and may derive the parameter value on the basis of the derived feature amount.

In the image processing apparatus according to the present disclosure, the plurality of radiographic images may be of the breast as an object and the feature amount may be an amount of mammary gland of the breast.

In the image processing apparatus according to the present disclosure, the plurality of radiographic images may be of the breast as an object and the derivation unit may derive the parameter value on the basis of a mammary gland region and a fat region of the breast in the projection image which is the image analysis result.

In the image processing apparatus according to the present disclosure, the plurality of radiographic images may be of the breast as an object and the derivation unit may derive the parameter value on the basis of a contrast value of a local region corresponding to the mammary gland of the breast which is the image analysis result.

In the image processing apparatus according to the present disclosure, at least one of the plurality of projection images may be a projection image obtained in a case in which the incident angle of the radiation with respect to the radiation detector is 0 degrees.

In order to achieve the object, according to the present disclosure, there is provided an image processing method comprising: generating a tomographic image from a plurality of projection images, which have been captured by a radiation detector at each of a plurality of imaging positions with different irradiation angles, with radiation sequentially emitted from each of the plurality of imaging positions, using a reconstruction process; deriving a parameter value used in predetermined image processing which is performed on the tomographic image, on the basis of an image analysis result of at least one of the plurality of projection images; correcting the parameter value according to image processing used in the reconstruction process; and performing the predetermined image processing on the tomographic image using the corrected parameter value.

In order to achieve the object, according to the present disclosure, there is provided an image processing method comprising: generating a tomographic image from a plurality of projection images, which have been captured by a radiation detector at each of a plurality of imaging positions with different irradiation angles, with radiation sequentially emitted from each of the plurality of imaging positions, using a reconstruction process; deriving a parameter value used in predetermined image processing which is performed on the tomographic image, on the basis of an image analysis result after image processing used in the reconstruction process is performed on at least one of the plurality of projection images; and performing the predetermined image processing on the tomographic image using the parameter value.

In order to achieve the object, according to the present disclosure, there is provided an image processing program that causes a computer to perform: generating a tomographic image from a plurality of projection images, which have been captured by a radiation detector at each of a plurality of imaging positions with different irradiation angles, with radiation sequentially emitted from each of the plurality of imaging positions, using a reconstruction process; deriving a parameter value used in predetermined image processing which is performed on the tomographic image, on the basis of an image analysis result of at least one of the plurality of projection images; correcting the parameter value according to image processing used in the reconstruction process; and performing the predetermined image processing on the tomographic image using the corrected parameter value.

In order to achieve the object, according to the present disclosure, there is provided an image processing program that causes a computer to perform: generating a tomographic image from a plurality of projection images, which have been captured by a radiation detector at each of a plurality of imaging positions with different irradiation angles, with radiation sequentially emitted from each of the plurality of imaging positions, using a reconstruction process; deriving a parameter value used in predetermined image processing which is performed on the tomographic image, on the basis of an image analysis result after image processing used in the reconstruction process is performed on at least one of the plurality of projection images; and performing the predetermined image processing on the tomographic image using the parameter value.

According to the present disclosure, it is possible to prevent the deterioration of the image quality of a tomographic image.

DETAILED DESCRIPTION

Hereinafter, embodiments of the invention will be described in detail with reference to the drawings. The embodiments do not limit the invention.

First Embodiment

In this embodiment, a radiography system that captures a radiographic image of the breast of a subject which is an example of an object will be described in detail.

Figure 1:
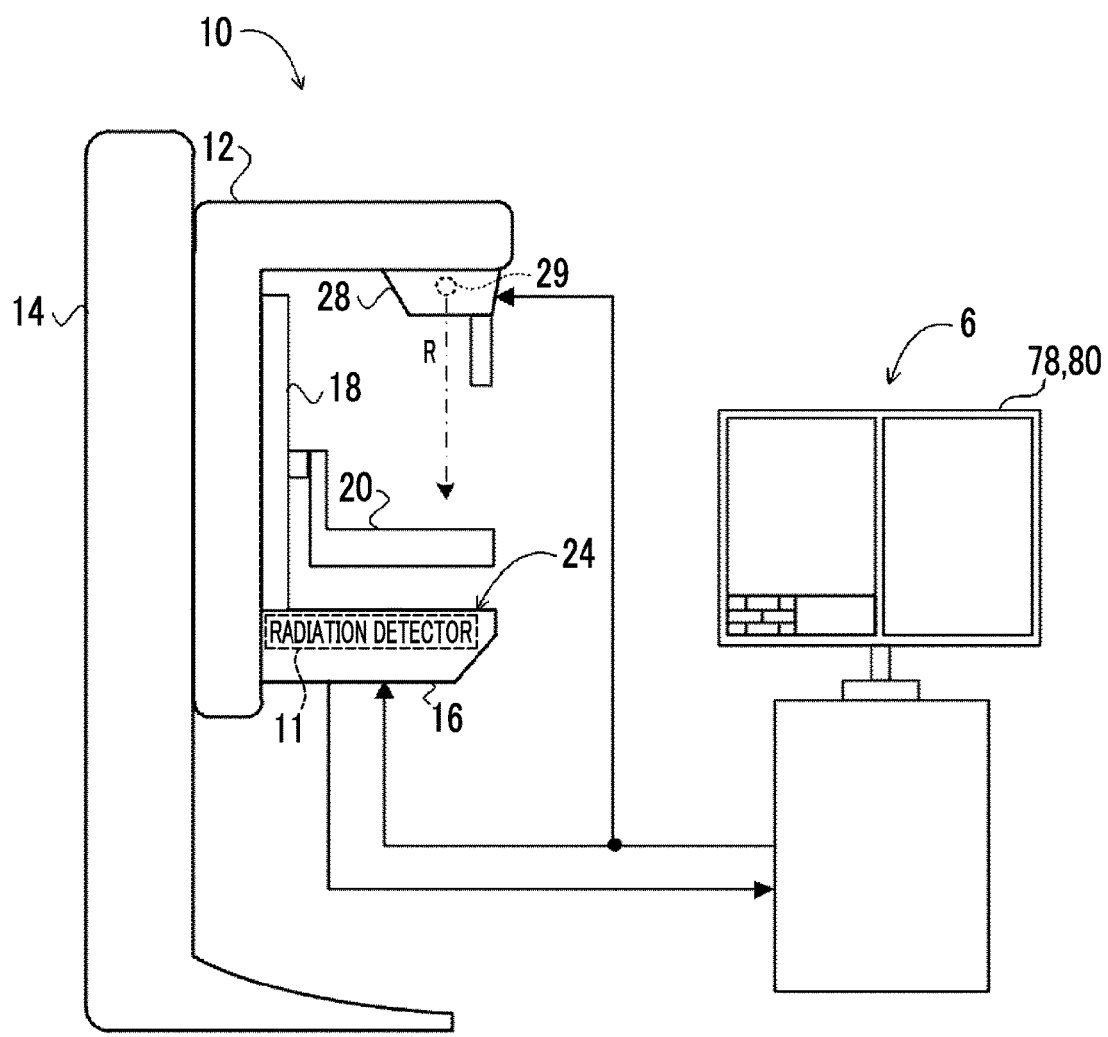
FIG. 1 is a configuration diagram illustrating an example of the overall configuration of a radiography system according to a first embodiment.

First, an example of the overall configuration of the radiography system according to this embodiment will be described. FIG. 1 is a configuration diagram illustrating an example of the overall configuration of a radiography system 1 according to this embodiment.

As illustrated in FIG. 1, the radiography system 1 according to this embodiment includes a console 6 and a mammography apparatus 10. In the radiography system 1 according to this embodiment, a user, such as a doctor or a radiology technician, operates the mammography apparatus 10 to capture the radiographic image of the breast of the subject on the basis of a command (imaging order) input from an external system (for example, a radiology information system (RIS)) through the console 6.

Figure 2:
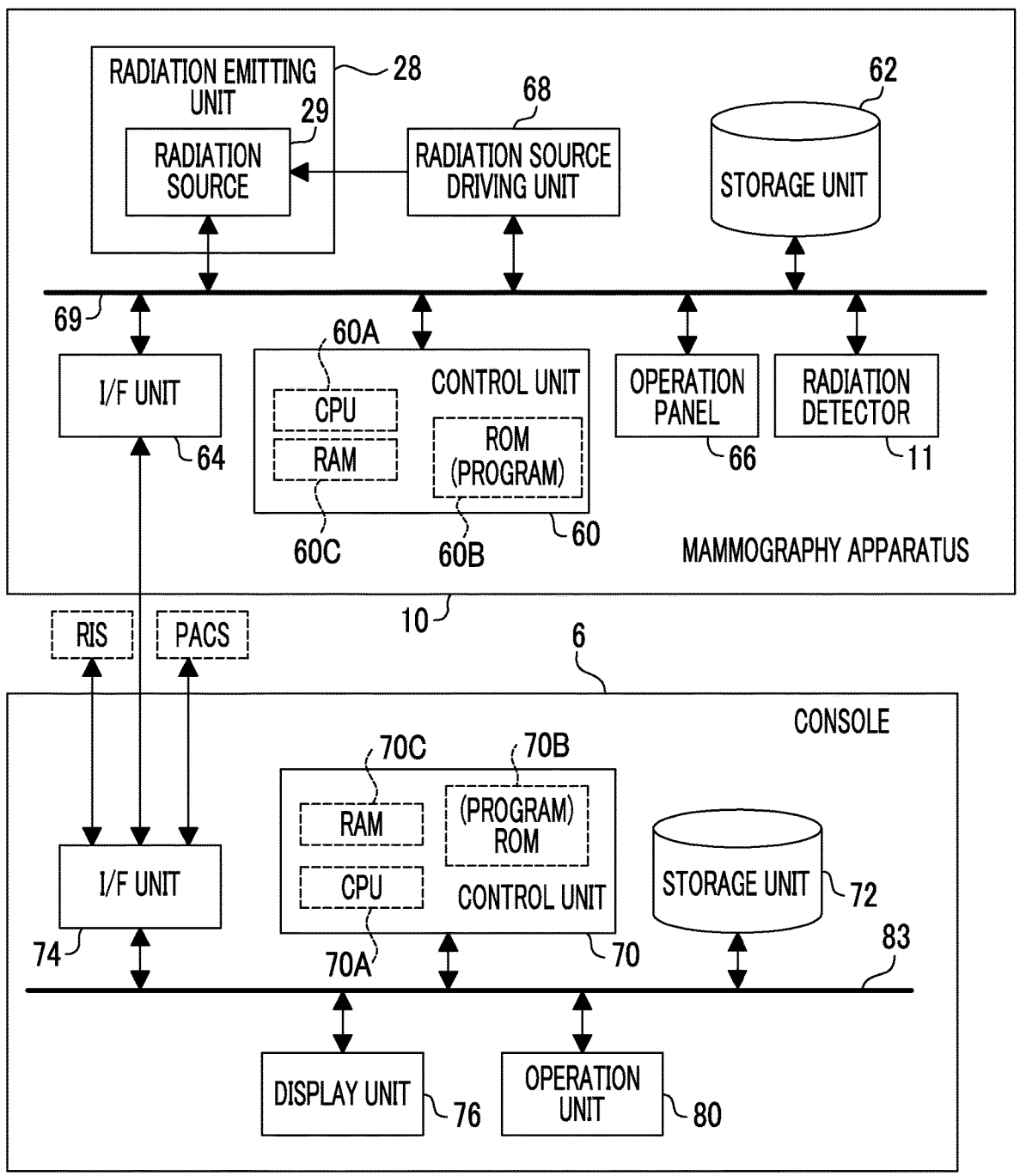
FIG. 2 is a block diagram illustrating an example of the configuration of a console and a mammography apparatus according to the first embodiment.

FIG. 2 is a block diagram illustrating an example of the configuration of the console 6 and the mammography apparatus 10 according to this embodiment. Hereinafter, the console 6 and the mammography apparatus 10 according to this embodiment will be described with reference to FIGS. 1 and 2.

The mammography apparatus 10 according to this embodiment is an apparatus that irradiates the breast compressed by a compression plate 20 with radiation R (for example, X-rays) and captures the radiographic image of the breast. In addition, the mammography apparatus 10 may be an apparatus that captures an image of the breast of the subject in a state (seated state) in which the subject sits down on a chair (including a wheelchair) as well as a state (standing state) in which the subject stands up. The mammography apparatus 10 may be any apparatus that can capture the radiographic image of at least the breast of the subject.

In addition, the mammography apparatus 10 according to this embodiment has a function of performing so-called tomosynthesis imaging (which will be described in detail below) and simple imaging.

A holding portion 18 of the mammography apparatus 10 supports an imaging table 16 provided in an imaging unit 12 and a radiation source 29 in a state in which an imaging surface 24 and the radiation source 29 provided in a radiation emitting unit 28 are separated by a predetermined distance.

A radiation detector 11 that detects the radiation R transmitted through the breast and the imaging surface 24 of the imaging table 16 is provided in the imaging table 16. The mammography apparatus 10 generates a radiographic image on the basis of the radiation R detected by the radiation detector 11. However, the type of radiation detector 11 is not particularly limited. For example, the radiation detector 11 may be an indirect-conversion-type radiation detector that converts the radiation R into light and converts the converted light into charge or a direct-conversion-type radiation detector that directly converts the radiation R into charge. In this embodiment, image data indicating the radiographic image output from the radiation detector 11 of the mammography apparatus 10 is transmitted to the console 6.

A shaft (not illustrated) is provided in the imaging unit 12 of the mammography apparatus 10 such that the imaging unit 12 can be rotated with respect to a base portion 14. The shaft is fixed to a support portion 22 and the shaft and the support portion 22 are integrally rotated.

Gears (not illustrated) are provided in the shaft provided in the imaging unit 12 and the holding portion 18. The gears can switch between an engaged state and a disengaged state to switch an operation state between a state in which the holding portion 18 and the shaft are connected and are integrally rotated and a state in which the shaft is separated from the holding portion 18 and idles. In a case in which tomosynthesis imaging is performed, the shaft is separated from the holding portion 18 and idles. Means for switching between the transmission and non-transmission of the power of the shaft is not limited to the gear and various mechanical elements may be used.

As illustrated in FIG. 2, the mammography apparatus 10 according to this embodiment includes the radiation detector 11, the radiation emitting unit 28, a control unit 60, a storage unit 62, an interface (I/F) unit 64, an operation panel 66, and a radiation source driving unit 68. The radiation detector 11, the radiation source 29, the control unit 60, the storage unit 62, the I/F unit 64, the operation panel 66, and the radiation source driving unit 68 are connected to each other through a bus 69 such as a system bus or a control bus.

The control unit 60 according to this embodiment includes a central processing unit (CPU) 60A, a read only memory (ROM) 60B, and a random access memory (RAM) 60C. The CPU 60A controls the overall operation of the mammography apparatus 10 in response to a command from the console 6. For example, various programs including an image processing program (which will be described below) executed by the CPU 60A are stored in the ROM 60B in advance. The RAM 60C temporarily stores various kinds of data.

For example, the image data of the radiographic image captured by the radiation detector 11 and various kinds of information are stored in the storage unit 62. Examples of the storage unit 62 include a hard disk drive (HDD) and a solid state drive (SSD). The I/F unit 64 transmits and receives various kinds of information to and from the console 6 using at least one of wireless communication or wired communication. For example, the operation panel 66 is provided as a plurality of switches in the imaging table 16 of the mammography apparatus 10. In addition, the operation panel 66 may be provided as a touch panel.

The radiation source driving unit 68 rotates the shaft (not illustrated) provided in the imaging unit 12 to continuously move the radiation source 29 of the radiation emitting unit 28 such that the radiation source 29 is moved to a plurality of imaging positions with different irradiation angles in tomosynthesis imaging. In this embodiment, as illustrated in FIG. 3, the radiation source driving unit 68 moves the radiation source 29 to the imaging positions where the irradiation angles of the radiation emitting unit 28 are different from each other and which are spaced a predetermined angle θ apart, that is, the positions where the incident angles of the radiation R with respect to the radiation detector 11 are different from each other.

Figure 3:
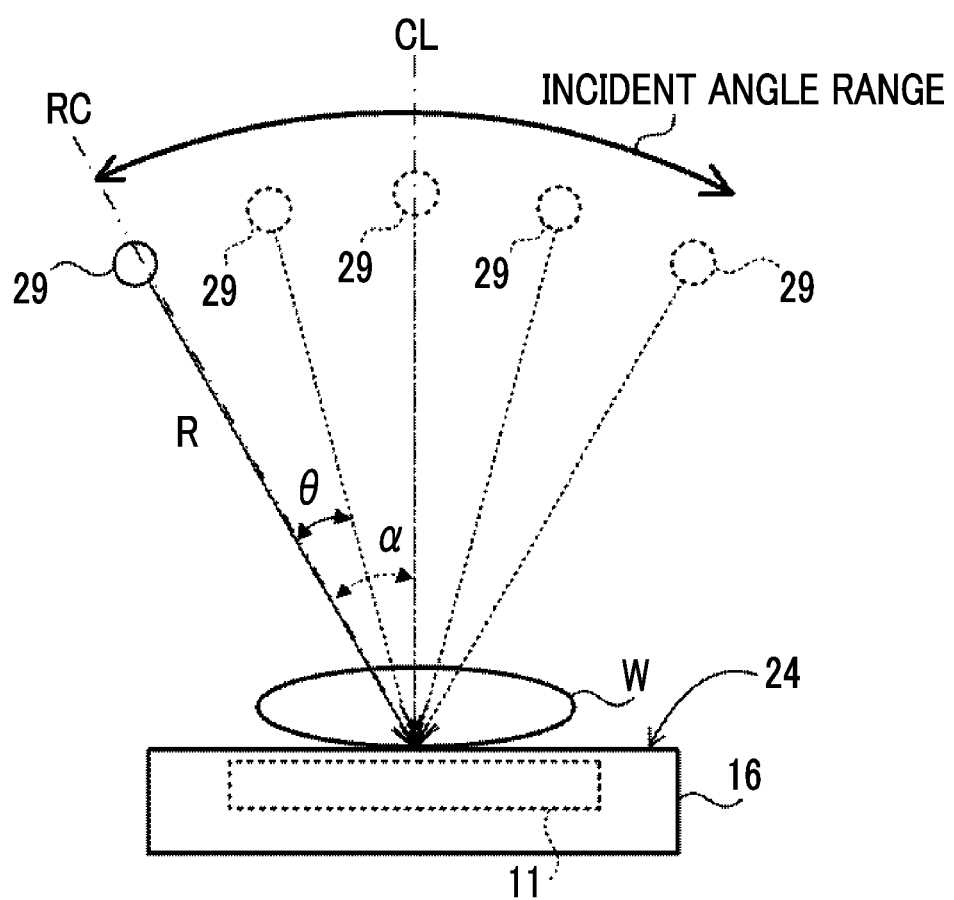
FIG. 3 is a diagram illustrating tomosynthesis imaging performed by the mammography apparatus according to the first embodiment.

As illustrated in FIG. 3, the incident angle means an angle α formed between a line CL normal to a detection surface of the radiation detector 11 and a radiation axis RC. Here, it is assumed that the detection surface of the radiation detector 11 is substantially parallel to the imaging surface 24. Hereinafter, as illustrated in FIG. 3, a predetermined range in which the incident angles (irradiation angles) are different from each other in tomosynthesis imaging is referred to as an "incident angle range". An example of the incident angle range is a range of ±10 degrees or ±20 degrees with respect to the line CL normal to the detection surface of the radiation detector 11.

The console 6 according to this embodiment controls the mammography apparatus 10, using, for example, an imaging order or various kinds of information acquired from an external system, such as an RIS, through a wireless communication local area network (LAN).

As illustrated in FIG. 2, the console 6 according to this embodiment includes a control unit 70, a storage unit 72, an I/F unit 74, a display unit 76, and an operation unit 80. The control unit 70, the storage unit 72, the I/F unit 74, the display unit 76, and the operation unit 80 are connected to each other through a bus 83 such as a system bus or a control bus.

The control unit 70 according to this embodiment controls the overall operation of the console 6. The control unit 70 according to this embodiment includes a CPU 70A, a ROM 70B, and a RAM 70C. The CPU 70A controls the overall operation of the mammography apparatus 10 in response to a command from the console 6. For example, various programs including an image processing program (which will be described below) executed by the CPU 70A are stored in the ROM 70B in advance. The RAM 70C temporarily stores various kinds of data.

For example, the image data of the radiographic image captured by the mammography apparatus 10 and various kinds of information are stored in the storage unit 72. Examples of the storage unit 72 include an HDD and an SSD.

The I/F unit 74 transmits and receives various kinds of information to and from the mammography apparatus 10 or external systems, such as an RIS and a picture archiving and communication system (PACS), using at least one of wireless communication or wired communication.

The display unit 76 displays, for example, information related to imaging and the captured radiographic image. The operation unit 80 is used by a user to input, for example, a command to capture a radiographic image and a command related to image processing on the captured radiographic image. For example, the operation unit 80 may have the form of a keyboard or the form of a touch panel integrated with the display unit 76.

Next, the operation of the console 6 in the radiography system 1 according to this embodiment will be described. In general, predetermined image processing, such as a frequency enhancement process or a gradation process, is performed on the radiographic image to be interpreted by the user in order to assist the interpretation. The console 6 according to this embodiment performs the above-mentioned predetermined image processing (hereinafter, referred to as "image processing for a tomographic image") for a tomographic image. In general, a frequency enhancement process corresponding to the amount of mammary gland is performed on the radiographic image of the breast. Therefore, hereinafter, for example, a case in which the predetermined image processing is the frequency enhancement process will be described.

As the operation of the console 6, an operation in a case in which image processing is performed on the radiographic image obtained by tomosynthesis imaging will be described below. Hereinafter, the radiographic images captured by the radiation detector 11 at a plurality of imaging positions with different irradiation angles are referred to as projection images in tomosynthesis imaging. In addition, in a case in which a tomographic image reconstructed from the projection images and the projection images are generically referred to without being distinguished from each other, they are simply referred to as "radiographic images".

Figure 4:
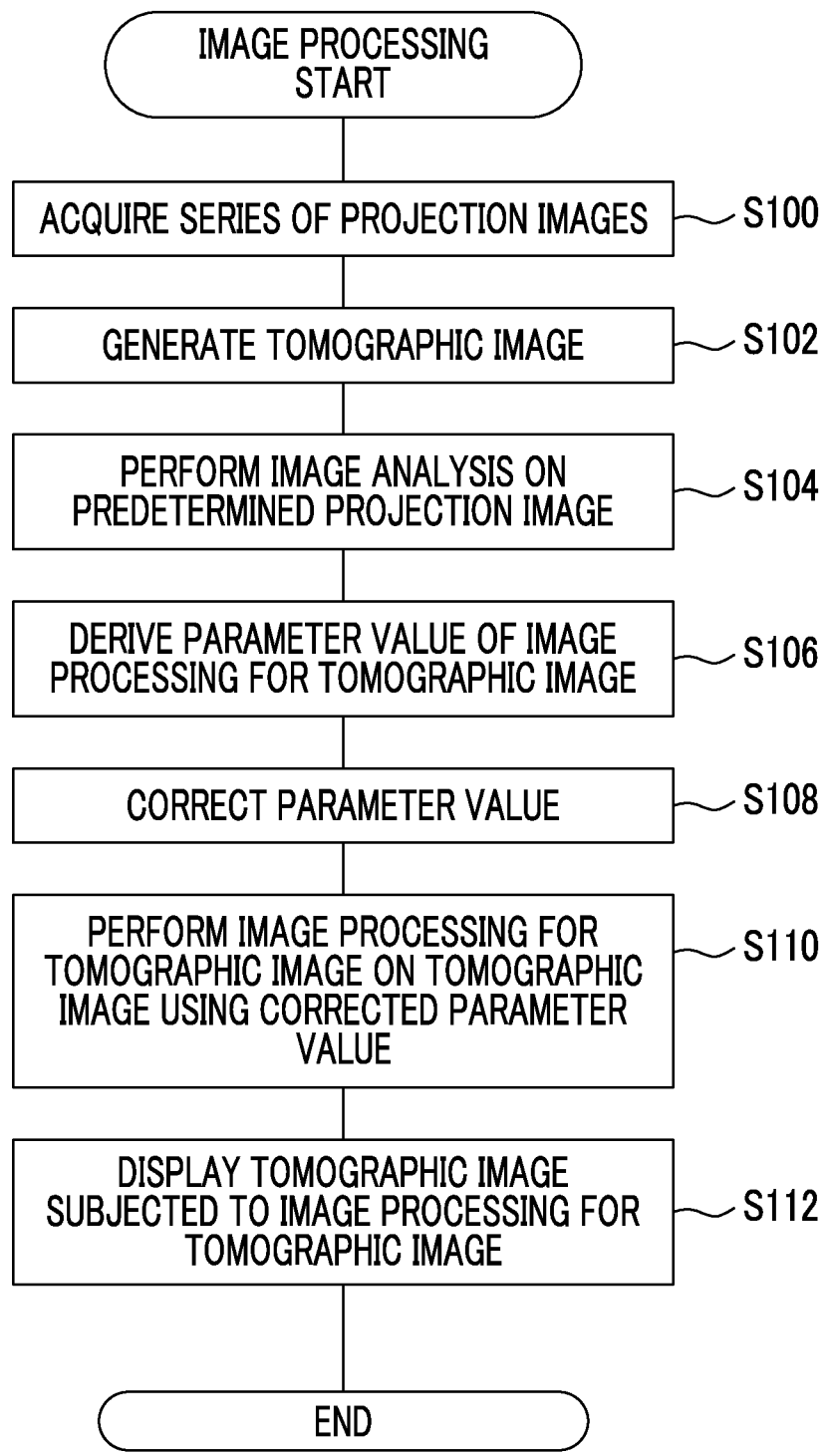
FIG. 4 is a flowchart illustrating an example of the flow of image processing in the console according to the first embodiment.
Figure 5:
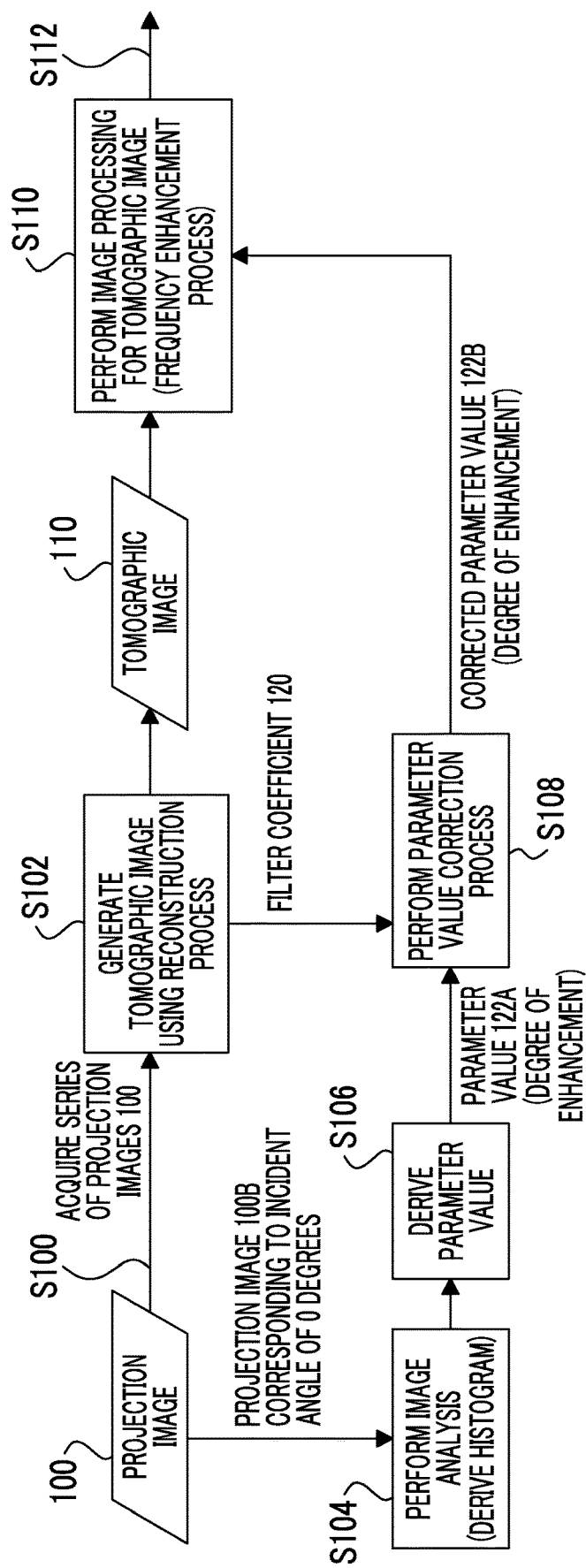
FIG. 5 is a flow diagram schematically illustrating the flow of image processing in a case in which image processing for a tomographic image according to the first embodiment is a frequency enhancement process.

FIG. 4 is a flowchart illustrating an example of the flow of image processing performed by the console 6 according to this embodiment. FIG. 5 is a flow diagram schematically illustrating the flow of image processing in a case in which the image processing for a tomographic image is the frequency enhancement process.

For example, in a case in which the console 6 according to this embodiment receives a command to display a tomographic image from the user through the operation unit 80 of the console 6, the CPU 70A of the control unit 70 executes the image processing program stored in the ROM 70B to perform the image processing illustrated in FIG. 4.

As illustrated in FIGS. 4 and 5, in Step S100, the control unit 70 acquires a series of projection images 100 obtained by one tomosynthesis imaging operation. The acquisition destination of the projection images is not particularly limited as long as it is a device storing a desired projection image and may be, for example, any one of the storage unit 72 of the host apparatus, the mammography apparatus 10, and a PACS.

Then, in Step S102, the control unit 70 generates a tomographic image 110 from the series of projection images 100 acquired in Step S100 using a reconstruction process. For example, the control unit 70 according to this embodiment performs a scattered ray removal process of removing a scattered ray component on each of the series of projection images 100. Then, the control unit 70 calculates the amount of movement of an interest of object between the series of projection images 100 on the basis of the incident angle of the radiation R at each imaging position where each projection image has been captured and reconstructs the tomographic image 110 using a so-called filtered back projection method (FBP).

The slice thickness of the generated tomographic image 110 is any slice thickness and may be a predetermined thickness or may be designated by the user. In addition, the number of tomographic images 110 to be generated may be predetermined and the slice thickness corresponding to the thickness of the breast compressed by the compression plate 20 and the number of tomographic images 110 to be generated may be used.

Then, in Step S104, the control unit 70 performs image analysis corresponding to the image processing for a tomographic image on a predetermined projection image among the series of projection images 100. For example, in this embodiment, the predetermined projection image is a projection image 100B corresponding to an incident angle of 0 degrees.

In this embodiment, as described above, the image processing for a tomographic image is the frequency enhancement process. In the frequency enhancement process, the degree of enhancement is used as a parameter value. The degree of enhancement is determined on the basis of a cumulative histogram of the pixel values of the radiographic image. Here, the control unit 70 derives the cumulative histogram of the pixel values of the projection image 100B using image analysis.

Then, in Step S106, the control unit 70 derives a parameter value 122A of the image processing for a tomographic image. In this embodiment, the degree of enhancement is derived as the parameter value 122A.

It has been known that, in a case in which the amount of mammary gland is different, the frequency of low-concentration data increases as the amount of mammary gland increases in pixel data of the radiographic image. In a case in which the frequency of the histogram of the pixel values are cumulatively added from the low-concentration side and the amount of mammary gland is large, that is, the frequency of low-concentration data is high, a cumulative value increases rapidly. In contrast, in a case in which the amount of mammary gland is small, the cumulative value increases gradually. Therefore, the amount of mammary gland can be determined to be large in a case in which a signal value with a predetermined cumulative frequency (x %) is close to the low-concentration side and can be determined to be small in a case in which the signal value is close to the high-concentration side.

For this reason, the control unit 70 analyzes the cumulative histogram of the image data of the projection image and derives a signal value with a predetermined cumulative frequency (x %) as a feature amount indicating a difference in the shape of the cumulative histogram depending on the amount of mammary gland. For example, the control unit 70 compares the derived signal with reference values that have been predetermined so as to correspond to three mammary gland amount categories, that is, large, medium, and small categories, and classifies the signal value into three categories, that is, small, medium, and large categories. Then, the control unit 70 selects the degree of enhancement of the frequency enhancement process corresponding to the classification results of the signal value from high, medium, and low levels and derives the degree of enhancement.

Then, in Step S108, the control unit 70 corrects the parameter value 122A derived in Step S106 according to image processing (hereinafter, referred to as "image processing corresponding to reconstruction") corresponding to the reconstruction process used to generate the tomographic image in Step S102. In this embodiment, the reconstruction process is performed using the FBP method as described above. Therefore, the control unit 70 corrects the parameter value 122A according to a filter coefficient 120 of a filter used in the FBP method.

Then, in Step S110, the control unit 70 performs the image processing for a tomographic image on the tomographic image 110 generated in Step S102 using the corrected parameter value 122B. In this embodiment, the control unit 70 performs the frequency enhancement process on the tomographic image 110 using the corrected parameter value 122B as the degree of enhancement.

Then, in Step S112, the control unit 70 displays the tomographic image 110 subjected to the image processing for a tomographic image on the display unit 76 and ends the image processing. The tomographic image that has been subjected to the frequency enhancement process according to a difference in the amount of mammary gland is displayed on the display unit 76 by the image processing.

As such, in the console 6 according to this embodiment, the control unit 70 functions as a generation unit that generates the tomographic image 110 from a plurality of projection images 100A, which have been captured by the radiation detector 11 at each of a plurality of imaging positions with different irradiation angles, with the radiation R sequentially emitted the plurality of imaging positions, using the reconstruction process. In addition, the control unit 70 functions as a derivation unit that derives the degree of enhancement as the parameter value used in the frequency enhancement process which is an example of the image processing for a tomographic image, on the basis of the image analysis result of the projection image 100B corresponding to an irradiation angle of 0 degrees. Furthermore, the control unit 70 functions as a correction unit that corrects the parameter value according to the image processing used in the reconstruction process and an image processing unit that performs the image processing for a tomographic image on the tomographic image using the corrected parameter value.

In general, in tomosynthesis imaging, the irradiation angle of radiation is limited. Therefore, for example, in a case in which the projection images are superimposed by the FBP method using the reconstruction process to reconstruct the tomographic image, an artifact which is a virtual image of a structure is likely to be included in a region in which no structures are originally present in the object. Specifically, in some cases, back projection causes an artifact to be included in a region in which no structures are originally present in a tomographic image of a tomographic plane different from the tomographic image of the tomographic plane in which a structure is present. This phenomenon occurs due to other reconstruction processing methods in addition to the FBP method.

Therefore, in a case in which image analysis is performed on the tomographic image in order to perform predetermined image processing such as a frequency enhancement process, it is difficult to obtain accurate analysis results.

For this reason, the control unit 70 of the console 6 according to this embodiment performs image analysis on the projection image and derives the parameter value of the image processing for a tomographic image on the basis of the image analysis results.

Here, in the image processing for a tomographic image performed on the tomographic image, in a case in which the parameter value derived from the projection image is used without any change, the tomographic image is affected by image processing, such as a filtering process, used in the reconstruction process for generating a tomographic image from a projection image. Therefore, in some cases, the image processing for a tomographic image is not appropriately performed.

In contrast, the control unit 70 of the console 6 according to this embodiment corrects the parameter value according to image processing used in the reconstruction process and performs the image processing for a tomographic image on the tomographic image 110 using the corrected parameter value.

Therefore, according to the console 6 of this embodiment, it is possible to prevent the deterioration of the image quality of the tomographic image 110.

In this embodiment, the aspect in which the image processing for a tomographic image is a frequency enhancement process and the parameter value is the degree of enhancement derived from the cumulative histogram derived by performing image analysis on the projection image 100B has been described. However, the image processing for a tomographic image is not particularly limited.

Figure 6:
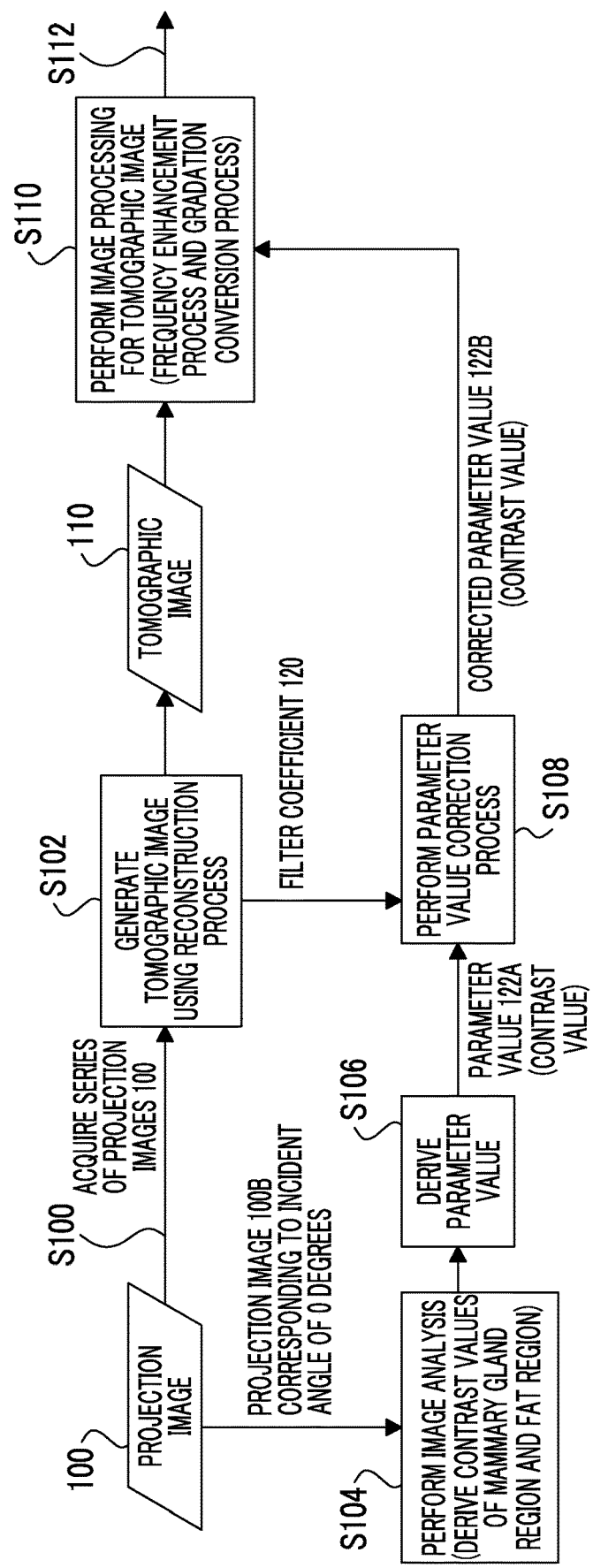
FIG. 6 is a flow diagram schematically illustrating the flow of image processing in a case in which the image processing for a tomographic image according to the first embodiment is the frequency enhancement process and a gradation conversion process.

For example, in general, the mammographic image in which the amount of mammary gland is large has a lower contrast and is more likely to be a blurred image than the mammographic image in which the amount of mammary gland is small. Therefore, a technique has been known which performs a frequency enhancement process and a gradation conversion process as the image processing for a tomographic image on the basis of a contrast value in order to easily distinguish the mammary gland tissues from the fat tissues. As such, in a case in which the frequency enhancement process and the gradation conversion process are performed as the image processing for a tomographic image, as illustrated in FIG. 6, in Step S104, the control unit 70 performs image analysis on the projection image 100B to detect a local region corresponding to the mammary gland in the mammographic image as a mammary gland region (low-concentration region) and derives the contrast values of the detected mammary gland region and a fat region (high-concentration region). Then, the control unit 70 obtains the contrast value as the parameter value 122A in Step S106 and corrects the parameter value 122A using the filter coefficient 120 in Step S108. In Step S110, the control unit 70 performs the image processing for a tomographic image using the corrected parameter value 122B, adjusts the contrast of the mammary gland region (low-concentration region) using the gradation conversion process, and enhances the contrast of the fat region (high-concentration region) using the frequency enhancement process.

Second Embodiment

Next, a second embodiment will be described in detail. In this embodiment, the same configuration and operation as those described in the first embodiment are denoted by the same reference numerals and the detailed description thereof will not be repeated.

Since the configuration of the radiography system 1 and the configuration of the console 6 and the mammography apparatus 10 are the same as those in the first embodiment, the description thereof will not be repeated. In this embodiment, image processing performed by the control unit 70 of the mammography apparatus 10 is different from the image processing (see FIG. 4) according to the first embodiment in some processes. Therefore, different processes will be described.

Figure 7:
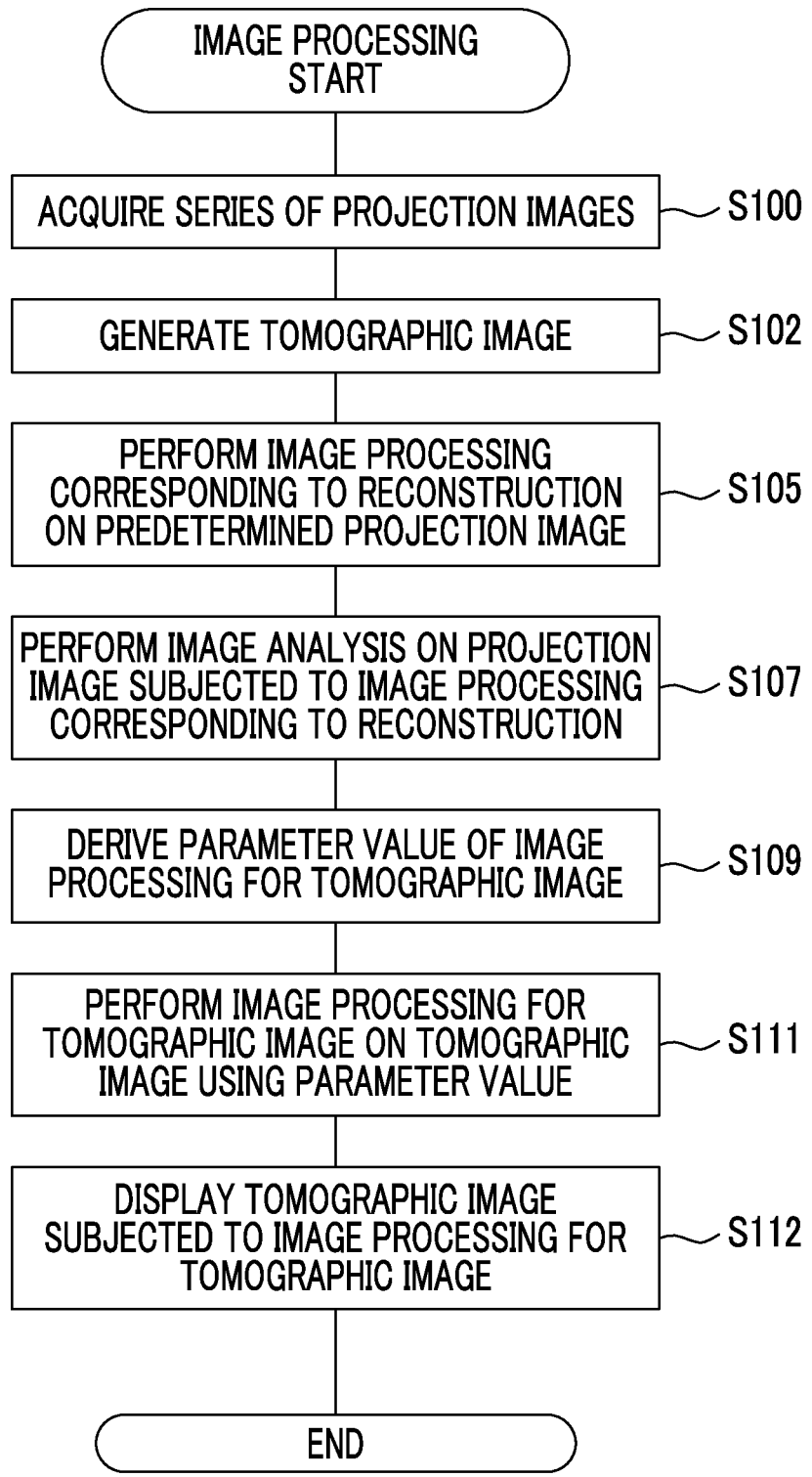
FIG. 7 is a flowchart illustrating an example of the flow of image processing in a console according to a second embodiment.
Figure 8:
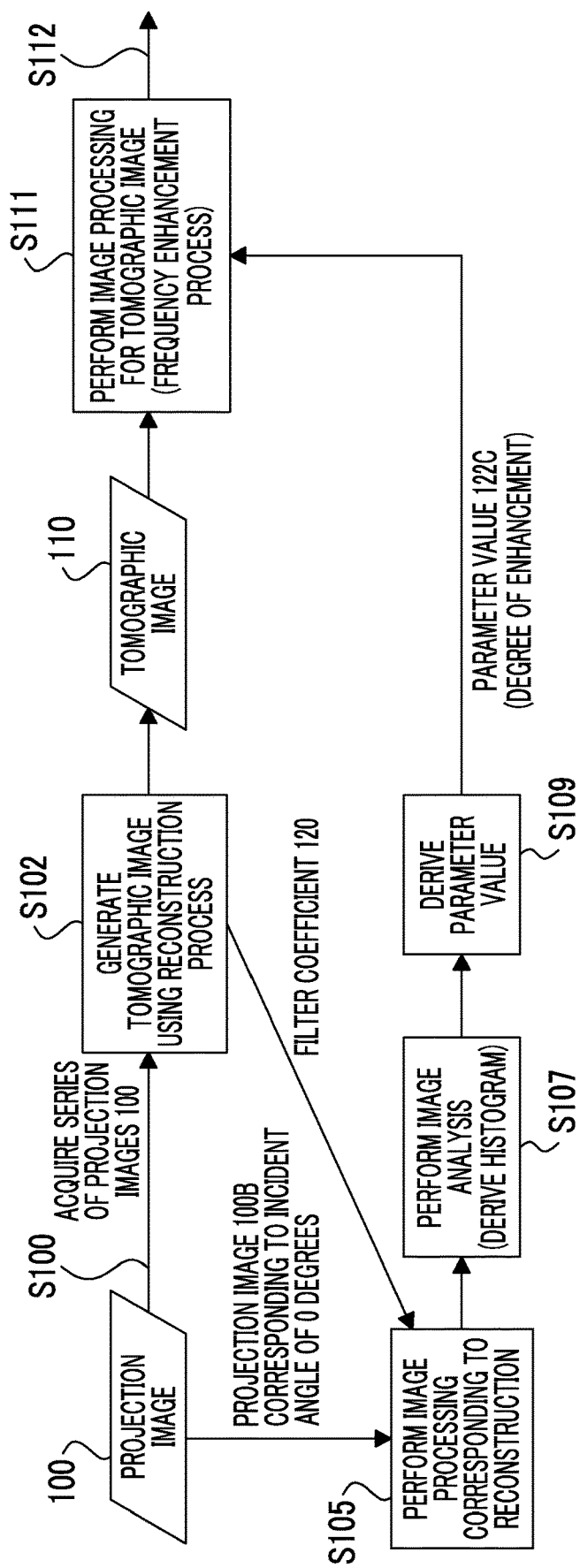
FIG. 8 is a flow diagram schematically illustrating the flow of image processing in a case in which image processing for a tomographic image according to the second embodiment is a frequency enhancement process.

FIG. 7 is a flowchart illustrating an example of the flow of image processing in the console 6 according to this embodiment. FIG. 8 is a flow diagram schematically illustrating the flow of image processing in a case in which the image processing for a tomographic image is a frequency enhancement process.

The image processing illustrated in FIG. 7 differs from the image processing (see FIG. 4) according to the first embodiment in that a process from Step S105 to Step S111 is performed instead of the process from Step S104 to Step S110. Therefore, different processes will be described.

In Step S105, the control unit 70 performs image processing corresponding to reconstruction on the tomographic image 110 obtained by performing the process in Step S102 on a predetermined projection image among a series of projection images 100. For example, in this embodiment, the predetermined projection image is the projection image 100B corresponding to an incident angle of 0 degrees as in the first embodiment. The image processing corresponding to reconstruction according to this embodiment is image processing corresponding to a filter coefficient used in the reconstruction process.

Then, in Step S107, the control unit 70 performs image analysis on the projection image 100B subjected to the image processing corresponding to reconstruction in Step S105 as in Step S104 (see FIG. 4) of the image processing according to the first embodiment.

Then, in Step S109, the control unit 70 derives the degree of enhancement as the parameter value 122C of the image processing for a tomographic image as in Step S106 (see FIG. 4) of the image processing according to the first embodiment.

Then, in Step S111, the control unit 70 performs the image processing for a tomographic image on the tomographic image 110 using the parameter value 122B derived in Step S109 as in Step S110 of the image processing according to the first embodiment.

As described above, in this embodiment, the frequency enhancement process is performed on the tomographic image 110 using the corrected parameter value 122B which is the degree of enhancement.

As such, in the console 6 according to this embodiment, the control unit 70 functions as a generation unit that generates the tomographic image 110 from a plurality of projection images 100A, which have been captured by the radiation detector 11 at each of a plurality of imaging positions with different irradiation angles, with the radiation R sequentially emitted from each of the plurality of imaging positions, using the reconstruction process. In addition, the control unit 70 functions as a derivation unit that derives the degree of enhancement as the parameter value 122C used in the frequency enhancement process which is an example of the image processing for a tomographic image, on the basis of the image analysis result after image processing corresponding to the filtering process used in the reconstruction process is performed on the projection image 100B corresponding to an irradiation angle of 0 degrees. Furthermore, the control unit 70 functions as an image processing unit that performs the image processing for a tomographic image on the tomographic image 110 using the parameter value 122C.

As described in the first embodiment, an artifact is generated in the tomographic image. Therefore, in a case in which image analysis is performed on the tomographic image in order to perform predetermined image processing such as a frequency enhancement process, accurate analysis results may not be obtained.

For this reason, the control unit 70 of the console 6 according to this embodiment performs image processing corresponding to the filtering process used in the reconstruction process on the projection image, performs image analysis, and derives the parameter value of the image processing for a tomographic image on the basis of the image analysis result. Therefore, it is possible to derive the parameter value considering the reconstruction process in the generation of a tomographic image.

Therefore, according to the console 6 of this embodiment, it is possible to prevent the deterioration of the image quality of the tomographic image 110.

In each of the above-described embodiments, the case in which the FBP method is used as the reconstruction processing method for generating a tomographic image has been described. However, the reconstruction processing method is not limited to the FBP method. As the reconstruction processing method, known reconstruction processing methods, such as an algebraic reconstruction method, and successive approximation reconstruction method, may be used in addition to a computed tomography (CT) reconstruction processing method such as a shift-and-add method. In a case in which any reconstruction processing method is used, image processing required for the reconstruction process is performed. Therefore, this image processing may be performed as the image processing corresponding to reconstruction.

In each of the above-described embodiments, the aspect in which image analysis is performed on the projection image 100B corresponding to an incident angle of 0 degrees among a series of projection images 100 obtained by tomosynthesis imaging and the parameter value is derived has been described. However, the projection image used to derive the parameter value is not limited thereto. For example, a representative value (for example, an average value) of the parameter values obtained by performing image analysis on a plurality of projection images 100 may be derived. In this case, the plurality of projection images 100 may be, for example, all of the series of projection images 100B or may be the projection images captured at the imaging positions at the center (an incident angle of 0 degrees) and both ends of the incident angle range.

In each of the above-described embodiments, the aspect in which the object is the breast has been described. However, the object is not limited to the breast and may be other parts such as the lung. For example, in a case in which the object is the lung and a frequency enhancement process is performed as the image processing for a tomographic image on a tomographic image for diagnosing a lung cancer in order to make a lung field clear, the technique according to the present disclosure may be applied. In addition, in a case in which the image processing for a tomographic image is performed in order to easily distinguish bone tissues from soft tissues, the technique according to the present disclosure may be applied.

In each of the above-described embodiments, various processors other than the CPU may perform the image processing performed by the execution of software (program) by the CPU. In this case, examples of the processor include a programmable logic device (PLD) whose circuit configuration can be changed after manufacture, such as a field-programmable gate array (FPGA), and a dedicated electric circuit, such as an application specific integrated circuit (ASIC), which is a processor having a dedicated circuit configuration designed to perform a specific process. In addition, the image processing may be performed by one of the various processors or may be performed by a combination of two or more processors of the same type or different types (for example, a combination of a plurality of FPGAs and a combination of a CPU and an FPGA). Specifically, the hardware structure of the various processors is an electric circuit obtained by combining circuit elements such as semiconductor elements.

In each of the above-described embodiments, the aspect in which various programs stored in the control unit 60 of the mammography apparatus 10 and the control unit 70 of the console 6 are stored (installed) in the ROMs (60B and 70B) of the control unit 60 and the control unit 70 in advance has been described. However, the invention is not limited thereto. The image processing program may be recorded on a recording medium, such as a compact disk read only memory (CD-ROM), a digital versatile disk read only memory (DVD-ROM), or a universal serial bus (USB) memory, and then provided. In addition, the image processing program may be downloaded from an external apparatus through the network.

In each of the above-described embodiments, the radiation is not particularly limited. For example, X-rays or y-rays may be applied.

In addition, for example, the configuration and operation of the radiography system 1, the console 6, and the mammography apparatus 10 according to each of the above-described embodiments are illustrative and may be changed according to the situation, without departing from the scope and spirit of the invention. In addition, the above-described embodiments may be appropriately combined with each other.

What is claimed is:

1. An image processing apparatus comprising:
   at least one processor configured to:
   generate a tomographic image from a plurality of projection images, which have been captured by a radiation detector at each of a plurality of imaging positions with different irradiation angles, with radiation sequentially emitted from each of the plurality of imaging positions, using a reconstruction process;
   derive a parameter value used in predetermined image processing which is performed on the tomographic image, on the basis of an image analysis result of at least one of the plurality of projection images;
   correct the parameter value according to image processing used in the reconstruction process; and
   perform the predetermined image processing on the tomographic image using the parameter value corrected by the correction unit.

2. The image processing apparatus according to claim 1, wherein the reconstruction process is performed by a filtered back projection method, and
   the image processing used in the reconstruction process is a filtering process in the filtered back projection method.

3. The image processing apparatus according to claim 1, wherein the predetermined image processing is at least one of a frequency enhancement process or a gradation conversion process.

4. The image processing apparatus according to claim 1, wherein the at least one processor is configured to derive a feature amount from a cumulative histogram which is the image analysis result and to derive the parameter value on the basis of the derived feature amount.

5. The image processing apparatus according to claim 4, wherein the plurality of radiographic images are of the breast as an object, and
   the feature amount is an amount of mammary gland of the breast.

6. The image processing apparatus according to claim 1, wherein the plurality of radiographic images are of the breast as an object, and
   the at least one processor is configured to derive the parameter value on the basis of a mammary gland region and a fat region of the breast in the projection image which is the image analysis result.

7. The image processing apparatus according to claim 1, wherein the plurality of radiographic images are of the breast as an object, and
   the at least one processor is configured to derive the parameter value on the basis of a contrast value of a local region corresponding to the mammary gland of the breast which is the image analysis result.

8. The image processing apparatus according to claim 1, wherein at least one of the plurality of projection images is a projection image obtained in a case in which the incident angle of the radiation with respect to the radiation detector is 0 degrees.

9. An image processing method comprising:
   generating a tomographic image from a plurality of projection images, which have been captured by a radiation detector at each of a plurality of imaging positions with different irradiation angles, with radiation sequentially emitted from each of the plurality of imaging positions, using a reconstruction process;
   deriving a parameter value used in predetermined image processing which is performed on the tomographic image, on the basis of an image analysis result of at least one of the plurality of projection images;
   correcting the parameter value according to image processing used in the reconstruction process; and
   performing the predetermined image processing on the tomographic image using the corrected parameter value.

10. A non-transitory computer-readable storage medium that stores an image processing program that causes a computer to perform:
    generating a tomographic image from a plurality of projection images, which have been captured by a radiation detector at each of a plurality of imaging positions with different irradiation angles, with radiation sequentially emitted from each of the plurality of imaging positions, using a reconstruction process;
    deriving a parameter value used in predetermined image processing which is performed on the tomographic image, on the basis of an image analysis result of at least one of the plurality of projection images;
    correcting the parameter value according to image processing used in the reconstruction process; and
    performing the predetermined image processing on the tomographic image using the corrected parameter value.

* * * * *